(12) United States Patent
Trueba et al.

(10) Patent No.: US 11,066,347 B2
(45) Date of Patent: Jul. 20, 2021

(54) PURIFICATION AND LIQUEFACTION OF BIOGAS BY COMBINATION OF A CRYSTALLIZATION SYSTEM WITH A LIQUEFACTION EXCHANGER

(71) Applicant: L'Air Liquide, Societe Anonyme pour l'Etude et l'Exploitation des Procedes Georges Claude, Paris (FR)

(72) Inventors: Antonio Trueba, Les Loges en Josas (FR); Jorge Ernesto Tovar Ramos, Les Loges en Josas (FR); Frederic Crayssac, Les Loges en Josas (FR); Solene Valentin, Sassenage (FR); Marine Andrich, Les Loges en Josas (FR)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 16/840,036

(22) Filed: Apr. 3, 2020

(65) Prior Publication Data

US 2020/0317591 A1 Oct. 8, 2020

(30) Foreign Application Priority Data

Apr. 4, 2019 (FR) ...................... 1903602

(51) Int. Cl.
*B01D 7/02* (2006.01)
*C07C 7/14* (2006.01)
*F25J 3/06* (2006.01)

(52) U.S. Cl.
CPC ................. *C07C 7/14* (2013.01); *B01D 7/02* (2013.01); *F25J 3/0625* (2013.01); *F25J 3/0635* (2013.01)

(58) Field of Classification Search
CPC ........ B01D 2256/245; B01D 2257/504; B01D 53/002; B01D 2252/204; B01D 2256/22; B01D 2257/304; B01D 2257/55; B01D 2257/708; B01D 2257/80; B01D 2258/05; B01D 2259/65; B01D 53/02; B01D 53/1475; B01D 53/229; B01D 53/261; B01D 53/265; B01D 53/75; B01D 7/02;
(Continued)

(56) References Cited

U.S. PATENT DOCUMENTS

2020/0096254 A1\* 3/2020 Cardon .................... F25J 3/061

FOREIGN PATENT DOCUMENTS

| CN | 102 628 635 | 8/2012 |
| EP | 2 277 614 | 1/2011 |

(Continued)

OTHER PUBLICATIONS

French Search Report and Written Opinion for FR 1903602, dated Feb. 11, 2020. (Machine Translation).

*Primary Examiner* — Sharon Pregler
(74) *Attorney, Agent, or Firm* — Christopher J. Cronin

(57) ABSTRACT

Plant and process for the production of liquid methane from a feed gas stream comprising at least methane and carbon dioxide. A feed gas stream is injected into a $CO_2$ crystallizer in countercurrent fashion against a stream of predominantly liquid methane, thereby crystallizing amounts of carbon dioxide from the feed gas stream. Gaseous methane recovered from the $CO_2$ crystallizer is liquefied at a liquefaction exchanger.

17 Claims, 1 Drawing Sheet

(58) Field of Classification Search
CPC .... F25J 3/0266; F25J 2215/04; F25J 2220/66; F25J 3/067; F25J 1/0022; F25J 1/005; F25J 1/0238; C07C 7/005; C07C 7/10; C07C 7/12; C07C 7/14; C07C 7/144

See application file for complete search history.

(56) References Cited

FOREIGN PATENT DOCUMENTS

| FR | 3 050 655 | 11/2017 |
| JP | 2009 019192 | 1/2009 |
| WO | WO 2016/79115 | 11/2016 |

* cited by examiner

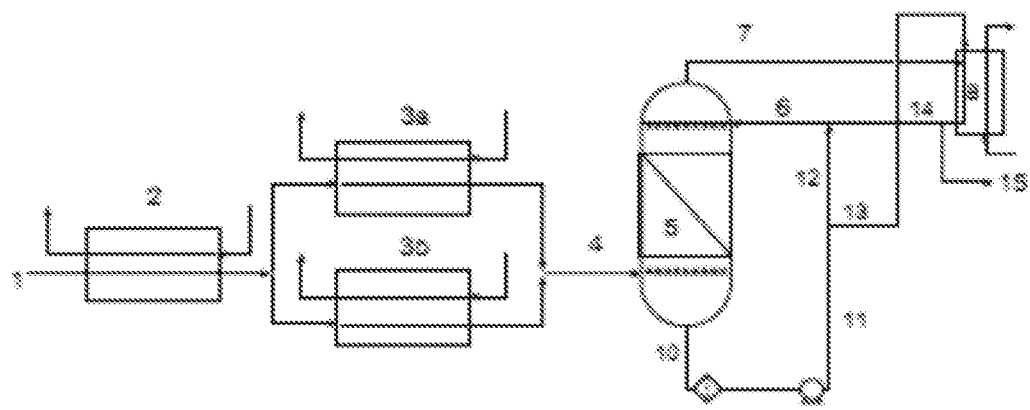

PURIFICATION AND LIQUEFACTION OF BIOGAS BY COMBINATION OF A CRYSTALLIZATION SYSTEM WITH A LIQUEFACTION EXCHANGER

CROSS-REFERENCE TO RELATED APPLICATIONS

This application claims the benefit of priority under 35 U.S.C. § 119 (a) and (b) to French patent application No. FR 1 903 602, filed Apr. 4, 2019, the entire contents of which are incorporated herein by reference.

BACKGROUND

Field of the Invention

The present invention relates to a plant and to a process for the production of liquid methane from a feed gas stream comprising at least methane and carbon dioxide. It relates in particular to a plant and to a process for the production of liquid methane from biogas.

Related Art

Biogas is the gas produced during the decomposition of organic matter in the absence of oxygen (anaerobic fermentation), also known as methanization. This can be natural decomposition—it is thus observed in marshland or in household waste landfills—but the production of biogas can also result from the methanization of waste in a dedicated reactor, known as methanizer or digester.

Due to its main constituents—methane and carbon dioxide—biogas is a powerful greenhouse gas; at the same time, it also constitutes a source of renewable energy which is appreciable in the context of the increasing scarcity of fossil fuels.

Biogas predominantly contains methane ($CH_4$) and carbon dioxide ($CO_2$), in proportions which can vary according to the way in which it is obtained, but also contains, in smaller proportions, water, nitrogen, hydrogen sulfide, oxygen, and also other organic compounds, in the form of traces.

Depending on the organic matter which has been decomposed and on the techniques used, the proportions of the components differ but, on average, biogas comprises, on a dry gas basis, from 30% to 75% of methane, from 15% to 60% of $CO_2$, from 0% to 15% of nitrogen, from 0% to 5% of oxygen and trace compounds.

Biogas is made use of economically in various ways. It can, after a gentle treatment, be made use of economically close to the production site in order to supply heat, electricity or a mixture of both (cogeneration); the high carbon dioxide content reduces its calorific value, increases the costs of compression and of transportation and limits the economic advantage of making use of it economically to this use nearby.

More intensive purification of biogas allows it to be more widely used; in particular, intensive purification of biogas makes it possible to obtain a biogas which has been purified to the specifications of natural gas and which can be substituted for the latter; biogas thus purified is known as "biomethane". Biomethane thus supplements natural gas resources with a renewable part produced within territories; it can be used for exactly the same uses as natural gas of fossil origin. It can feed a natural gas network or a vehicle filling station; it can also be liquefied to be stored in the form of liquefied natural gas (LNG), and the like.

In numerous regions of Europe and throughout the world, the natural gas network is not always accessible close to the areas of production of fermentable waste. Furthermore, while there is no need for heat on the biogas production site, depending on the purchase price of electricity, the cogeneration does not always have a sufficient output to render profitable the major investment in a digestion unit. It is then advantageous in these two cases to transport the biogas to a distribution or consumption point. The liquefaction of biogas after purification would make it possible to transport biomethane at a lower cost.

Today, processes for the purification of biogas are mainly based on the principles of absorption, permeation or adsorption. These systems then require the addition of a supplementary module in order to obtain biomethane in the liquid form. Moreover, in the majority of cases, the $CO_2$ content of biogas on conclusion of this purification stage is still too high to feed such liquefaction systems.

Starting from this, one problem which is posed is that of providing a single plant for the separation and liquefaction of methane resulting from a gas stream comprising at least methane and carbon dioxide, the gas stream preferably being biogas, the aim being to obtain liquid methane, preferably liquid biomethane, in order to make it easier to store and/or transport it.

SUMMARY OF THE INVENTION

A solution of the present invention is a plant for the production of liquid methane from a feed gas stream 1 comprising at least methane and carbon dioxide comprising, in the direction of circulation of the gas stream:
  a continuously operating system 5 for the crystallization of carbon dioxide comprising, countercurrentwise to the feed gas stream, the circulation of a stream 6 predominantly comprising liquid methane, and making possible the production of a methane-enriched gas stream 7, and
  an exchanger 8 for liquefaction of the methane-enriched gas stream 7 exiting from the crystallization system.

As the case may be, the plant according to the invention can exhibit one or more of the following characteristics:
  the said plant comprises, upstream of the crystallization system, a means C which makes it possible to bring the feed gas stream to a temperature of between −50° C. and −85° C., preferably between −57° C. and −75° C.;
  the feed gas stream comprises water and the means C comprises at least two exchangers 3a and 3b arranged in parallel, the exchangers each following a cycle comprising a production stage and a regeneration stage, with, at each moment of the cycle, an exchanger in the production stage and an exchanger in the regeneration stage;
  the plant comprises, upstream of the means C, a means C' 2 which makes it possible to bring the feed gas stream to a temperature of between 0° C. and 20° C., preferably of between 0° C. and 10° C.;
  the plant comprises a pipe connected to the lower bottom of the crystallization system, and a system for separation of liquid/solid phases placed on this pipe which makes it possible to recover $CO_2$ crystals;
  the feed stream is at a pressure of between atmospheric pressure and 20 bar, preferably between atmospheric pressure and 5 bar.

Another subject-matter of the present invention is a process for the production of liquid methane from a feed gas stream comprising at least methane and carbon dioxide which employs a plant as defined above, the said process comprising:

- a continuous stage of crystallization of the carbon dioxide contained in the feed gas stream by injection of the latter into the system for the crystallization of carbon dioxide comprising, countercurrentwise to the feed gas stream, the circulation of a stream predominantly comprising liquid methane;
- a stage of recovery of gaseous methane in the upper part of the crystallization system;
- a stage of liquefaction of the recovered methane, by means of the liquefaction exchanger; and
- a stage of recovery of liquid methane at the outlet of the liquefaction exchanger.

As the case may be, the process according to the invention can exhibit one or more of the characteristics below:

- the feed gas stream comprises water and the said process comprises, before the crystallization stage: a stage of reducing the concentration of water included in the feed gas stream by lowering the temperature of the feed gas stream to a temperature of between −57° C. and −75° C.; and a stage of recovery of a feed gas stream depleted in water;
- the stage of reducing the concentration of water comprises a lowering of the temperature of the feed gas stream in two steps, a first step during which the temperature of the feed gas stream is lowered to a temperature of between 0° C. and 10° C., and a second step during which the temperature of the feed gas stream is lowered to a temperature of between −57° C. and −75° C.;
- during the crystallization stage, the ratio of the flow rate of the feed gas stream to the flow rate of the countercurrentwise liquid methane stream is such that the solid $CO_2$ particles formed are entrained towards the lower bottom of the crystallization system;
- downstream of the scrubbing column, a mixture of liquid methane and of solid $CO_2$ particles is recovered at the lower bottom of the crystallization system, the liquid and solid phases of the said mixture are separated so as to recover the solid $CO_2$ particles, and a stream exhibiting a carbon dioxide content of between 2 ppm and 1000 ppm, preferably between 5 ppm and 200 ppm, is recovered at the outlet of the separation of the phases;
- the stream exhibiting a carbon dioxide content of between 2 ppm and 1000 ppm, preferably between 5 ppm and 200 ppm, is recycled in the crystallization system and/or in the liquefaction exchanger;
- the solid $CO_2$ particles are used to contribute cold to the cooling cycle of the liquefaction exchanger;
- the liquid methane recovered at the outlet of the liquefaction exchanger is partially returned to the crystallization system;
- the feed gas stream is biogas;
- the feed gas stream is at a pressure of between atmospheric pressure and 20 bar, preferably between atmospheric pressure and 5 bar.

BRIEF DESCRIPTION OF THE FIGURES

FIG. 1 is a schematic of an embodiment of the invention.

DETAILED DESCRIPTION OF THE INVENTION

The invention will now be described in more detail using FIG. 1.

The water of the feed gas stream is first of all condensed. To do this, the feed gas stream 1 is, in a first step, brought to a temperature of between 0 and 10° C. (1° C., for example) by means of an exchanger 2, in order to condense a part of the water contained in the biogas and to remove it in the liquid state. This stage makes it possible to reduce the amount of solid to be removed in the downstream exchangers.

In a second step, the biogas is brought to a temperature of between −57° C. and −75° C. in order to remove the majority of water present and the impurities or contaminants of COV type present in the feed gas stream. Two exchangers 3a and 3b are placed in parallel in order to cool the biogas down to this temperature. The exchangers are regenerated once the solid is deposited on the walls. The cycle time of each exchanger comprises a production phase and a regeneration phase of between 10 min and 10 h, preferably of between 30 min and 2 h.

In the context of the invention, the first step and the second step are combined in a stage known as "reducing the concentration of water".

A gas stream 4 depleted in water and in impurities is recovered at the outlet of the exchangers. This gas stream 4 is subsequently injected into a crystallization system 5 countercurrentwise to a mixture 6 mainly comprising liquid methane. The gas in contact with the liquid will bring about the crystallization of the $CO_2$ contained in the gas as it is cooled (cooling between −50° C. and −163° C.). It should be noted that it will be possible to observe, at the same time but to a lesser extent, the crystallization of the $H_2S$ contained in the feed stream.

The ratio of the flow rate of the feed gas stream to the flow rate of the countercurrentwise liquid methane stream is such that the entrainment of the solid $CO_2$ particles towards the lower bottom of the crystallization system is ensured and that the gas at the top of the crystallization system contains virtually no $CO_2$. The excess liquid flow rate ensures in particular very good wetting of the entire surface present inside the column and used as "contactor" between the liquid and the gas. For example, it will be possible to use structured packings as contactor.

Gaseous methane 7 is thus recovered in the upper part of the crystallization system, which gaseous methane is sent to a liquefaction exchanger 8 so as to produce liquid methane. A part 14 of this liquid methane will be returned to the crystallization system and another part 15 of this liquid methane will be sent to the production of liquid methane.

A mixture 10 of liquid methane and of solid $CO_2$ particles is recovered at the outlet of the lower bottom of the crystallization system. The phases of the said mixture are separated so as to recover the solid $CO_2$ particles, and a stream of liquid methane 11 comprising between 2 ppm and 1000 ppm of $CO_2$, preferably between 5 ppm and 200 ppm of $CO_2$, is recovered at the outlet of the separation. It should be noted that it will be possible to carry out the phase separation by means of a filter or of several filters in parallel and in alternating operation, or any other liquid/solid separation system.

The liquid methane stream 11 recovered at the outlet of the filtration is, on the one hand, recycled 12 to the top of the crystallization system and, on the other hand, sent 13 to the exchanger for liquefaction of the methane in order to ensure wetting of the exchange surface and to prevent deposits of $CO_2$ crystals in the liquefaction exchanger.

The process according to the invention requires a frigorific power contribution in order to operate. This contribution can be produced in several ways (depending on the amount of liquid biomethane to be produced, for example). By way of example but not exclusively: 1. From a liquid nitrogen source 2. By a process of reverse Brayton type: In the latter case, a refrigerant (nitrogen or a nitrogen/helium mixture) is compressed, cooled and expanded in a turbine. This refrigerant is subsequently reheated countercurrentwise to the hot fluids (including the biogas) in the exchangers. It contributes the cold necessary for its cooling down to −75° C., on the one hand, and for the liquefaction of the methane vapour which exits from the crystallization system.

From a thermodynamic viewpoint, when the mixture mainly composed of $CO_2$ and methane is cooled, the $CO_2$ begins to solidify from the gas phase below a certain temperature threshold (direct change from vapour $CO_2$ to solid $CO_2$). The temperature for the appearance of the first solid $CO_2$ crystals is estimated at approximately −87° C. for 1 bara and 50 mol % of $CO_2$ (i.e. temperature lower than the outlet temperature of the 2 exchangers in parallel). As liquid outflow from the crystallization system, the solid $CO_2$ and the liquid phase are close to thermodynamic equilibrium. The solid is then filtered off upstream of the pump in order to retain only the liquid phase. Nevertheless, a small amount of solid $CO_2$ may again be formed in the presence of liquid methane in the liquid reflux exchanger. If need be, either two exchangers in parallel (one in production and another in regeneration) or a solid/liquid phase separation system may then be placed on the liquid biomethane product line.

It should be noted that the solid $CO_2$ recovered in the phase separation system can be used to contribute cold to the cooling cycle and to thus reduce the specific consumption of the cryo-solidification cycle.

It should be noted that the process described is designed to operate at low pressure between atmospheric pressure and 20 bar, preferably between atmospheric pressure and 5 bar.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A process for production of liquid methane from biogas that comprises methane, water, and carbon dioxide, said process comprising the steps of:
    condensing amounts of water from a biogas feed stream by lowering a temperature of the biogas feed gas stream in a condensing exchanger to a temperature of between −57° C. and −75° C.;
    recovering a water-depleted feed gas stream from the condensing exchanger having a water content lower than that of the raw feed gas stream;
    injecting the water-depleted feed gas stream into a bottom portion of a $CO_2$ crystallizer system;
    feeding a stream predominantly comprising liquid methane into a top portion of the $CO_2$ crystallizer countercurrentwise to the injected feed gas stream, thereby crystallizing amounts of $CO_2$ contained in the injected water-depleted feed gas stream;
    recovering gaseous methane from the upper portion of the $CO_2$ crystallizer;
    liquefying the recovered gaseous methane with liquefaction exchanger, a cooling power of the liquefaction exchanger being supplied by a refrigerant;
    recovering a stream of liquid methane at an outlet of the liquefaction exchanger; and
    filtering solid $CO_2$ particles from the recovered stream of liquid methane to produce a $CO_2$-depleted stream of liquid methane having a $CO_2$ content of between 2 ppm and 1000 ppm.

2. A plant for the production of liquid methane from a feed gas stream comprising at least methane and carbon dioxide, said plant comprising, in the direction of circulation of the gas stream:
    a continuously operating system for the crystallization of carbon dioxide in which a stream predominantly comprising liquid methane is circulated countercurrentwise to the feed gas stream, thereby producing a methane-enriched gas stream; and
    a liquefaction exchanger adapted and configured to liquefy the produced methane-enriched gas stream exiting from the crystallization system.

3. The plant of claim 2, further comprising, upstream of the crystallization system, at least two heat exchangers adapted and configured to bring the feed gas stream to a temperature of between −50° C. and −85° C.

4. The plant of claim 3, wherein the at least two exchangers are arranged in parallel and each following a cycle comprising a production stage and a regeneration stage, with, at each moment of the cycle, an exchanger in the production stage and an exchanger in the regeneration stage.

5. The plant of claim 3, further comprising, upstream of the at least two heat exchangers a water condensation exchanger adapted and configured to bring the feed gas stream to a temperature of between 0° C. and 20° C.

6. The plant of claim 2, further comprising:
a pipe connected to a bottom of the crystallization system; and
a filter disposed in the pipe adapted and configured to separate liquid and solid phases, thereby enabling recovery of $CO_2$ crystals.

7. A process for production of liquid methane from a feed gas stream that comprises methane and carbon dioxide using the plant of claim 2, said process comprising the steps of:
continuous crystallization of carbon dioxide contained in the feed gas stream by injection of the feed gas stream into the continuously operating system for the crystallization of carbon dioxide in which a stream predominantly comprising liquid methane is circulated countercurrentwise to the feed gas stream;
recovering gaseous methane in an upper part of the continuously operating system for the crystallization of carbon dioxide;
liquefying the recovered gaseous methane with the liquefaction exchanger; and
recovering liquid methane at an outlet of the liquefaction exchanger.

8. The process of claim 7, wherein the feed gas stream further comprises water and said process further comprises, before the crystallization stage, the steps of:
reducing a concentration of the water in the feed gas stream to produce a water-depleted feed stream by lowering a temperature of the feed gas stream to a temperature of between −57° C. and −75° C.; and
recovering the water-depleted feed gas stream.

9. The process of claim 8, wherein the temperature of the feed gas stream is lowered in a first step during which the temperature of the feed gas stream is lowered to a temperature of between 0° C. and 10° C. and in a second step during which the temperature of the feed gas stream is lowered to a temperature of between −57° C. and −75° C.

10. The process of claim 7, wherein, during said continuous crystallization, a ratio of a flow rate of the feed gas stream to a flow rate of the countercurrentwise liquid methane stream is such that solid $CO_2$ particles formed during said continuous crystallization are entrained towards the lower bottom of the continuously operating system for the crystallization of carbon dioxide.

11. The process of claim 9, further comprising the steps of:
recovering a mixture of liquid methane and solid $CO_2$ particles at the lower bottom of the crystallization system; and
separating the solid $CO_2$ particles from the liquid methane in the recovered mixture, thereby producing a stream of recovered liquid methane downstream of said separation that has a carbon dioxide content of between 2 ppm and 1000 ppm.

12. The process of claim 11, further comprising the step of recycling the stream of recovered liquid methane in the continuously operating system for the crystallization of carbon dioxide.

13. The process of claim 11 further comprising the step of recycling the stream of recovered liquid methane in the liquefaction exchanger.

14. The process of claim 11, wherein the separated solid $CO_2$ particles are used to contribute cold to a cooling cycle of the liquefaction exchanger.

15. The process of claim 7, wherein the stream of recovered liquid methane is partially returned to the continuously operating system for the crystallization of carbon dioxide.

16. The process of claim 7, wherein the feed gas stream is biogas.

17. The process of claim 7, wherein the feed gas stream is at a pressure of between atmospheric pressure and 20 bar.

* * * * *